United States Patent [19]

Sunkel et al.

[11] Patent Number: 5,177,211

[45] Date of Patent: Jan. 5, 1993

[54] 4-ALKYL-1,4-DIHYDROPYRIDINES WITH PAF-ANTAGONIST ACTIVITY

[75] Inventors: Carlos Sunkel; Miguel Fau De Casa-Juana; Luis Santos; Pilar Ortega; Jaime Priego; Mariano Sanchez-Crespo, all of Madrid, Spain

[73] Assignee: Alter, S.A., Madrid, Spain

[21] Appl. No.: 815,890

[22] Filed: Dec. 27, 1991

Related U.S. Application Data

[63] Continuation of Ser. No. 299,972, Jan. 19, 1989, abandoned.

Foreign Application Priority Data

Jan. 21, 1988 [DE] Fed. Rep. of Germany ....... 3801717

[51] Int. Cl.$^5$ .......................................... C07D 211/86
[52] U.S. Cl. ..................................... 546/321; 514/356
[58] Field of Search ........................................ 546/321

[56] References Cited

U.S. PATENT DOCUMENTS

4,256,749  3/1981  Hoistmann et al. ................. 546/321
4,532,248  7/1985  Franckowiak et al. ............. 546/116

FOREIGN PATENT DOCUMENTS

1108615  9/1981  Canada ................................ 546/321

OTHER PUBLICATIONS

Vigante et al. CA 96: 199478 X.
W. W. Muir In: "Calcium Regulation by Calcium Antagonists". Ed. by R. G. Rahwan and D. T. Witiak, Am. Chem. Soc. Symposium Series, 201, 39-71, 1982.
D. J. Triggle, D. A. Langs and R. A. Janis, Med. Res. Rev., 9: 123-180, 1989.
E. Rios and G. Brum, Nature, 325: 717-20, 1987.
E. Rios and G. Pizarro, News Physiol. Sci., 3: 223-227, 1988.
J. Casals-Stenzel and H. O. Heuer, Methods in Enzymology, 187: 455-65, 1990.
H. O. Heuer and W. S. Adamus, J. Lipid Mediators, 2: 202, 1990.
H. O. Heuer, J. Casals-Stenzel, G. Muacevic, I. Steller and K. H. Weber. IIIrd, International Conference on Platelet-Activating Factor and Structurally Related Alkyl Ether Lipids. Tokyo, 1989, Abst. 1-4 p. 96.
D. Hosford and P. Braquet, Progress in Med. Chem., 27: 325-80, 1990.

Primary Examiner—Jane T. Fan
Attorney, Agent, or Firm—Darby & Darby

[57] ABSTRACT

4-alkyl-1,4-dihyropyridines, with PAF-antagonist activity, of formula (I) wherein R is saturated $C_1$-$C_4$, R' is saturated $C_1$-$C_6$ alkyl which may be interrupted by an oxygen atom, or 2-tetrahydrofurfuryl and $R^2$ is saturated $C_1$-$C_4$ or phenyl, the compound wherein R is methyl, R' is ethyl and $R^2$ is phenyl remain excluded, are described.

The compounds (I) are prepared by: (a) reaction of (II) with (III); (b) reaction of (IV) with (V); (c) reaction of (VI) with (III) and with (VII); (d) reaction of (VIII) with (V) and with (VII); or (e) reaction of (VIII) with (VI) and with (VII) in the presence of ammonia. The compounds (I) are useful due to their antagonist activity of the platelet activating factor.

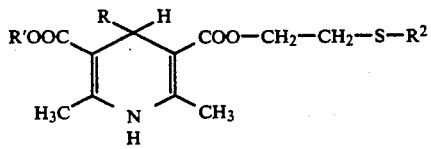

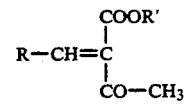

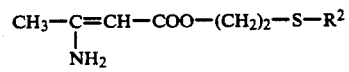

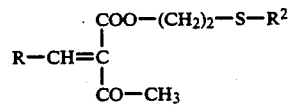

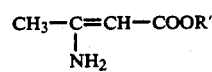

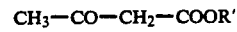

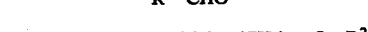

3 Claims, No Drawings

4-ALKYL-1,4-DIHYDROPYRIDINES WITH PAF-ANTAGONIST ACTIVITY

This is a continuation of application Ser. No. 07/299,972, filed Jan. 19, 1989 now abandoned.

The invention refers to a series of pharmaceutical compounds containing 1,4-dihydropyridines with an alkyl group in the 4-position of the ring, which have antagonist activity of the Platelet Activator Factor (PAF-aceter) and the methods of obtainment thereof.

The chemical structure of the PAF-aceter was identified as 1-O-hexadecyl/octadecyl-2-acetyl-sn-glycero-3-phosphocholine. This compound is a phospholipidc autokoide and an extremely powerful mediator of inflammatory reactions which is given off by various types of cells, human tissues and laboratory animals. These cells are mainly granulocytes, basophils, eosinophils and neutrophils, tissue macrophages and monocytes of the peripheral blood, platelets, glandular epithelial cells, endothelial cells and neuronic tissue. The PAF-aceter is a powerful inducer of platelet aggregation and secretion and a powerful hypotensor of the systemic circulation. This effect is due to its capacity to promote peripheral vasodilatation, but its actions also have an influence on lung and heart circulation, since it produces a reduction of the myocardial contractility and reduction of the coronary flow. Another effect of the PAF-aceter is that it induces bronchial constriction at a dosis 100 times lower than histamine.

Finally, the pro-inflammatory action thereof should be pointed out due to the capacity to stimulate the adhesion and aggregation of neutrophils followed by the release of lysosomal enzymes and activation of the cascade of arachidonic acid. In studies carried out on laboratory animals it has been demonstrated that PAF-aceter has an effect on vascular endothelium, promoting exudation of protein rich plasma and the adhesion of leukocytes. These data have been confirmed by experiments in which PAF-aceter was injected in the skin of healthy volunteers.

It may cause disorders of heart rate and the above mentioned reduction of contractile force of the heart. Concerning liver tissue it stimulates glycogenolysis at concentrations 10,000 times lower than those required of epinephrine and glucagon. More recently, actions on the central nervous system, on the physiology of reproduction and on immunoregulation have been described.

These facts, along with the demonstration of the existence of PAF-aceter in biological fluids in different experimental and clinical situations and the results obtained with the use of pharmacological antagonists in experimental models and in clinical studies, suggest a pathogenic role of PAF-aceter in certain human diseases.

On this basis, the specific inhibitors of biosynthesis and/or of the effects of PAF-aceter could represent a new type of therapeutic agents, especially in lung diseases such as bronchial asma, allegic pneumonitis and respiratory distress in adults, in which some PAF antagonists have demonstrated favourable effects in the first clinical tests carried out. Likewise, a series of PAF-aceter antagonists have reduced or put an end to reactions of anaphylaxis, hypersensitivity, endotoxic shock and gastric ulcerations in experimental studies. The participation of PAF-aceter in an entire series of pathological states based on immunoallergy such as inflammatory processes of the skin, psoriasis, glomerulonephritis and rejection of transplants.

Some compounds with antagonist activity of the PAF-aceter receptor which may be grouped into four basic types:
- Antagonists based on modifications of the chemical structure of PAF-aceter (structural analogues)
- Natural products and derivatives thereof
- Synthetic structures
- Already existing drugs and derivatives thereof, for example, certain benzodiazepins, allergy drugs, anti-inflammatories, adrenergic drugs.

Some antagonists of $Ca^{++}$ also have PAF antagonist properties, such as the case of Diltiazem and Gallopamil, however, not all $Ca^{++}$ channel blocking agents have this activity. Hence, 1,4-dihydropyridines, such as Nifedipin, only demonstrate a very weak activity, since the concentrations required to obtain an effect are 1,000,000 times higher than those that inhibit calcium flows in other cells, and, at least, 1,000 times higher than those of specific PAF-aceter antagonists.

Surprisingly, some 1,4-dihydropyridines which have an aliphatic group in the 4-position of the ring show a strong PAF-antagonist activity not described until now.

The object of the invention is, therefore, pharmaceutical compositions with PAF-antagonist activity which contain as active substances one or more compounds of general formula I

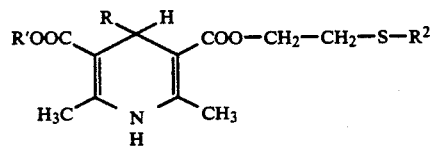

wherein

R is a $C_1$-$C_4$ saturated straight or branched chain alkyl group

R' may be a $C_1$-$C_6$ saturated straight or branched chain alkyl group, which may be interrupted by an oxygen atom, it may also represent the 2-tetrahydrofurfuryl group, $R^2$ may be a $C_1$-$C_4$ saturated straight chain alkyl group or may represent a phenyl group One of the compounds included in general formula I, when $R=CH_3$, $R'=CH_3-CH_2-$ and $R^2=$phenyl, is described in the bibliography (KHIM, GETEROTSIKL, SOEDIN., 219 (1982.))

The pharmacological activity of the compounds of formula I has been established as indicated hereafter.

The compounds can be obtained in accordance with the methods already known in literature.

Hence, a) A compound of formula II

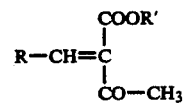

wherein R and R' are as defined above, is reacted with a compound of formula III

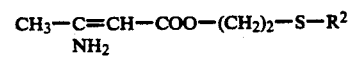

wherein $R^2$ is as defined above, to give a compound of formula I; or b) A compound of formula IV

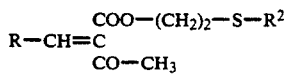  IV wherein R and $R^2$ are defined as above, is reacted with a compound of formula V

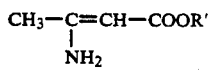  V wherein R' is as defined above, to give a compound of formula I; or c) A compound of formula VI $$CH_3-CO-CH_2-COOR' \quad VI$$

wherein R' is as defined above, is reacted with a compound of formula III, wherein $R^2$ is as defined above, and a compound of formula VII $$R-CHO \quad VII$$

wherein R is as defined above to give a compound of formula I; or d) A compound of formula VIII $$CH_3-CO-CH_2-COO-(CH_2)_2-S-R^2 \quad VIII$$

wherein $R^2$ is as defined above, is reacted with a compound of formula V, wherein R' is as defined above, and a compound of formula VII, wherein R is defined as above, to give a compound of formula I; or e) A compound of formula VIII, wherein $R^2$ is defined as above, is reacted with a compound of formula VI, wherein R' is defined as above, and a compound of formula VII, wherein R is defined as above, in the presence of ammonia, to give a compound of formula I.

The invention also refers to those embodiments of the process according to which one starts from a compound obtainable as an intermediate in any step of the process and the remaining steps of the process are carried out, or the process is interrupted in any step, or in which a starting product is formed under the reaction conditions or in which a reaction compound is present in the form of salts thereof.

The mixtures of diastereoisomers or enantiomers obtained can be separated thanks to the different physical-chemical properties of the components, by means of known methods, such as, for example, fractionated recrystallization and/or chromatography, by assymetric induction reactions or by means of the use of microorganisms.

The starting compounds are known, or in the event they are new, they can be obtained by known methods.

The compounds of formula I can be used as medication to be administered orally, rectally, topically, parenterally or inhalation, in the form of a pharmaceutical preparation which contains at least one of the compounds of formula I in combination with a pharmaceutically acceptable excipient. The pharmaceutical preparations may come, for example, in the form of tablets, sugar-coated pills, capsules, suppositories, syrups or aerosols. Of course, the amount of active compound is between 0.1 and 99% by weight of the preparation, preferably between 2 and 50% by weight in oral preparations. The daily dose of the active substance depends on the type of administration and, in general, between 25 and 100 mg. are administered orally, between 0.1 and 50 mg. per dose are administered intravenously or intramuscularly and solutions containing between 0.1 and 0.5% of the active product are used for inhalattions.

EXAMPLE 1

2-(ethylthio)ethyl-2,6-dimethyl-4-methyl-5-methoxycarbonyl-1,4-dihydropyridin-3-carboxylate

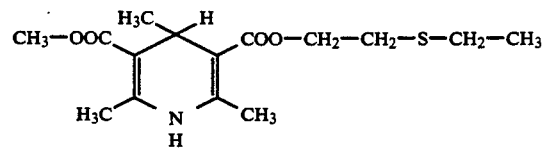

A mixture made up of 28.54 g (0.15 moles) of 2-(ethylthio)ethyl-acetylacetate, 17.27 g (0.15 moles) of methyl 3-aminocrotonate and 8.5 ml (6.61 g; 0.15 moles) of acetaldehyde in 120 ml. of ethanol, is heated to reflux with stirring during 8 hours. After cooling the resulting solution to −10° C., a light yellow solid is obtained; melting point: 84°-6° C. (recrystallized in ethanol.) The yield of the reaction is around 49%.

| Analysis for $C_{15}H_{23}NO_4S$ | | | | |
|---|---|---|---|---|
| | % C | % H | % N | % S |
| Calculated | 57.48 | 7.40 | 4.47 | 10.23 |
| Found | 57.37 | 7.61 | 4.60 | 10.34 |

I.R. spectrum (KBr) $\nu(cm^{-1})$: 3340, 3240, 2960, 1700, 1650, 1490, 1430, 1350, 1290, 1220, 1200, 1140, 1090, 1050, 770, 700.

NMR spectrum ($\delta$, $CDCl_3$) p.p.m.=6.3(1H, sa); 4.3 (2H, t); 3.9 to 3.7 (1H+3H, m+s); 2.9 to 2.4 (2H+2H, t+c); 2.3 (6H, s); 1.3 (3H, t); 1 (3H, d.).

EXAMPLE 2

2-(methylthio)ethyl-2,6-dimethyl-4-methyl-5-methoxycarbonyl-1,4-dihydropyridin-3-carboxylate

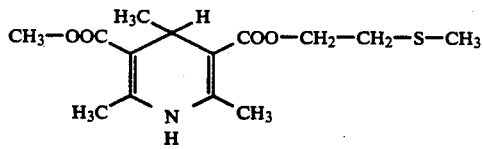

A mixture made up of 20 g (0.11 moles) of 2-(methylthio)ethyl-acetylacetate, 13.07 g (0.11 moles) of methyl 3-aminocrotonate and 6.42 ml (0.11 moles) of acetaldehyde in 110 ml of ethanol, is heated to reflux with stirring for 8 hours. After evaporation of 50 ml. of previous solvent and cooling the resulting solution to −10° C., a white solid is obtained; melting point: 92°-5° (recrystallization in ethanol.) The yield of the reaction is 47%.

| Analysis for $C_{14}H_{21}NO_4S$ | | | | |
|---|---|---|---|---|
| | % C | % H | % N | % S |
| Calculated | 56.17 | 7.07 | 4.68 | 10.71 |

-continued

| Analysis for $C_{14}H_{21}NO_4S$ | | | | |
|---|---|---|---|---|
| | % C | % H | % N | % S |
| Found | 55.85 | 7.36 | 4.76 | 11.03 |

I.R. spectrum (KBr) $\nu$(cm$^{-1}$): 3340, 2950, 2920, 1700, 1650, 1490, 1430, 1350, 1290, 1220, 1200, 1130, 1090, 1050, 980, 770, 700.

NMR spectrum ($\delta$, CDCl$_3$) p.p.m.=6.4 (1H, sa); 4.3 (2H, t); 3.8 to 3.6 (1H+3H, m+s); 2.7 (2H, t); 2.3 (6H, s); 2.1 (3H, s); 1 (3H, d.).

EXAMPLE 3

2-(methylthio)ethyl-2,6-dimethyl-5-ethoxycarbonyl-4-methyl-1,4-dihydropyridin-3-carboxylate

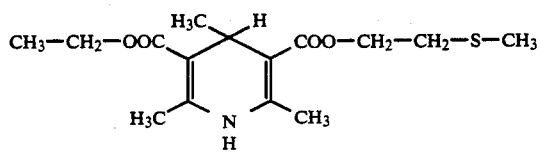

A mixture made up of 20 g (0.11 moles) of 2-(methylthio) ethyl-acetylacetate, 14.66 g (0.11 moles) of ethyl 3-aminocrotonate and 6.41 ml (5 g; 0.11 moles) of acetaldehyde in 110 ml. of ethanol, is heated to reflux with stirring for 8 hours. After evaporation of 50 ml. of the previous solvent and cooling the resulting solution to −10° C., a light yellow solid is obtained; melting point: 87°-90° C. (recrystallized in aqueous ethanol 70:30.)

| Analysis for $C_{15}H_{23}NO_4S$ | | | | |
|---|---|---|---|---|
| | % C | % H | % N | % S |
| Calculated | 57.48 | 7.40 | 4.47 | 10.23 |
| Found | 57.69 | 7.48 | 4.48 | 10.37 |

I.R. spectrum (KBr) $\nu$(cm$^{-1}$): 3340, 2950, 2920, 1700, 1650, 1490, 1370, 1300, 1210, 1130, 1090, 1050, 980, 770, 690.

NMR spectrum ($\delta$, CDCl$_3$) p.p.m.=6.6 (1H, sa); 4.4 to 3.7 (5H, m); 2.8 (2H, t); 2.3 (6H, s); 2.2 (3H, s); 1.3 (3H, t); 1 (3H, d.).

EXAMPLE 4

2-(ethylthio)ethyl-2,6-dimethyl-5-ethoxycarbonyl-4-methyl-1,4-dihydropyridin-3-carboxylate

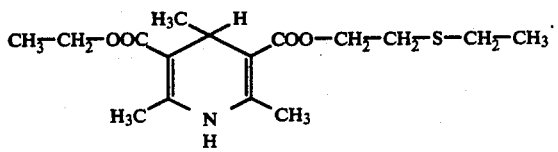

A mixture made up of 20 g (0.11 moles) of 2-(ethylthio) ethyl-acetylacetate, 13.58 g (0.11 moles) ethyl-3-aminocrotonate and 5.94 ml (4.63 g; 0.11 moles) of acetaldehyde in 100 ml of ethanol is heated to reflux with stirring for 8 hours. After evaporation of 50 ml. of the solvent and cooling the resulting solution to −10° C., a white solid is obtained; melting point: 83°-5° C. (recrystallized in ethyl acetate). The yield of the reaction is 53%.

| Analysis for $C_{16}H_{25}NO_4S$ | | | | |
|---|---|---|---|---|
| | % C | % H | % N | % S |
| Calculated | 58.69 | 7.70 | 4.28 | 9.79 |
| Found | 58.51 | 7.98 | 4.66 | 10.24 |

I.R. spectrum (KBr) $\nu$(cm$^{-1}$): 3380, 2980, 1710, 1650, 1490, 1380, 1300, 1220, 1140, 1100, 1060, 990, 780, 700.

NMR spectrum ($\delta$, CDCl$_3$) p.p.m.=6.5 (1H, sa); 4.4 to 3.7 (4H+4H, td+m); 2.6 (2H+2H, t+t); 2.2 (6H, s); 1.3 (6H, t); 1 (3H, d.).

EXAMPLE 5

2-(methylthio)ethyl-2,6-dimethyl-4-methyl-5-(2-methoxyethoxycarbonyl)-1,4-dihydropyridin-3-carboxylate

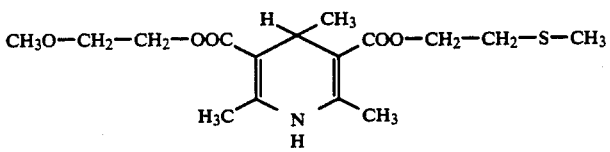

A mixture made up of 10.5 g (0.06 moles) of 2-(methylthio)ethyl-3-aminocrotonate and 11.16 g (0.06 moles) of 2-methoxyethyl-α-ethylidenacetylacetate in 60 ml. of ethanol is heated to reflux with stirring for 12 hours. After evaporation of the solvent at reduced pressure, dissolution of the residue in 20 ml. of ethyl acetate to boiling and cooling of the resulting solution to 5° C., a solid is obtained; melting point: 58°-60° C. (recrystallized in ethanol.) The yield of the reaction is 51%.

| Analysis for $C_{16}H_{25}NO_5S$ | | | | |
|---|---|---|---|---|
| | % C | % H | % N | % S |
| Calculated | 55.96 | 7.34 | 4.08 | 9.34 |
| Found | 56.16 | 7.65 | 3.98 | 9.68 |

I.R. spectrum (KBr) $\nu$(cm$^{-1}$): 3360, 2950, 1700, 1640, 1480, 1380, 1290, 1210, 1130, 1050, 980, 770, 690.

NMR spectrum ($\delta$, DMSO-D$_6$) p.p.m.=8.5 (1H, sa); 4.2 (4H, td); 3.8 to 3.4 (3H, m); 3.3 (3H, s); 2.7 (2H, t); 2.2 (6H, s); 2.1 (3H, s); 0.9 (3H, d.).

EXAMPLE 6

2-(methylthio)ethyl-2,6-dimethyl-4-ethyl-5-ethoxycarbonyl-1,4-dihydropyridin-3-carboxylate

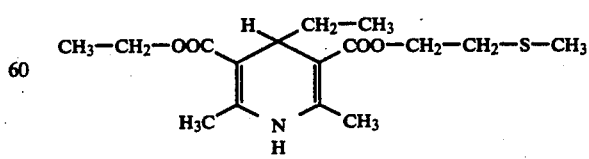

A mixture made up of 15 g (0.09 moles) of 2-(methylthio) ethyl-acetalacetate, 10.99 g (0.09 moles) of ethyl-3-aminocrotonate and 6.5 ml (4.94 g; 0.09 moles) of propionaldehyde in 85 ml. of ethanol, is heated to reflux with stirring for 10 hours. After evaporation of the solvent at reduced pressure, the residue is dissolved in 10 ml. of ethyl acetate to boiling and the resulting solution is cooled to −10° C. In this way a white solid is obtained; melting point: 96°-8° C. (recrystallized in DMF-H₂O.) The yield of the reaction is 65%.

| Analysis for C₁₆H₂₅NO₄S | | | | |
|---|---|---|---|---|
| | % C | % H | % N | % S |
| Calculated | 58.69 | 7.70 | 4.28 | 9.79 |
| Found | 58.94 | 8.00 | 4.21 | 9.80 |

I.R. spectrum (KBr) ν(cm⁻¹): 3360, 3240, 2980, 2940, 2880, 1700, 1660, 1490, 1450, 1380, 1220, 1140, 1080, 1010, 890, 790, 770, 730.

NMR spectrum (δ, CDCl₃) p.p.m.=6.9 (1H, s); 4.4 to 3.8 (5H, m); 2.7 (2H, t); 2.3 (6H, s); 2.2 (3H, s); 1.3 (5H, td); 0.8 (3H, t.).

EXAMPLE 7

2-(methylthio)ethyl-2,6-dimethyl-5-ethoxycarbonyl-4-n-propyl-1,4-dihydropyridin-3-carboxylate

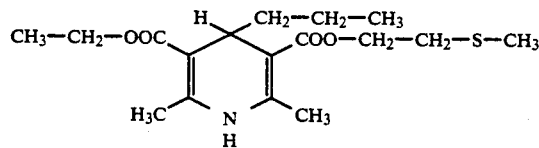

A mixture made up of 15 g (0.09 moles) of 2-(methylthio)ethyl-acetylacetate, 10.99 g (0.09 moles) of ethyl-3-aminocrotonate and 7.7 ml (6.14 g; (0.09 moles) of butyraldehyde in 85 ml. of absolute ethanol is heated to reflux with stirring for 10 hours. After evaporation of 45 ml of solvent at reduced pressure, the resulting solution is cooled to −10° C. In this way a pale yellow crystalline solid is obtained; melting point: 94°-96° C. (recrystallized in ethanol.) The yield of the reaction is 56%.

| Analysis for C₁₇H₂₇NO₄S | | | | |
|---|---|---|---|---|
| | % C | % H | % N | % S |
| Calculated | 59.80 | 7.97 | 4.10 | 9.39 |
| Found | 59.64 | 8.02 | 3.96 | 9.35 |

I.R. spectrum (KBr) ν(cm⁻¹): 3340, 3250, 2960, 2920, 1710, 1660, 1500, 1380, 1300, 1220, 1150, 1090, 1010, 800, 740, 680.

NMR spectrum (δ, CDCl₃) p.p.m.=6.5 (1H, sa); 4.4 to 3.8 (4H+1H,m); 2.7 (2H, t); 2.3 (6H, s); 2.1 (3H, s); 1.4 to 0.6 (10H, t+m.).

EXAMPLE 8

2-(ethylthio)ethyl-2,6-dimethyl-5-ethoxycarbonyl-4-n-propyl-1,4-dihydropyridin-3-carboxylate

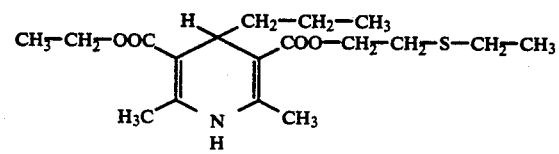

A mixture made up of 15 g (0.08 moles) of 2-(ethylthio) ethyl-acetylacetate, 10.18 g (0.08 moles) of ethyl-acetylacetate, 10.18 g (0.08 moles) of ethyl-3-aminocrotonate and 7.2 ml (5.69 g; 0.08 moles) of butyraldehyde in 80 ml of absolute ethanol, is heated to reflux with stirring for 10 hours. After evaporation of 40 ml of the solvent at reduced pressure and cooling of the resulting solution to −10° C., a crystalline yellow solid is prisms is obtained; melting point: 68°-70° C. (recrystallized in ethanol.) The yield of the reaction is 62%.

| Analysis for C₁₈H₂₉NO₄S | | | | |
|---|---|---|---|---|
| | % C | % H | % N | % S |
| Calculated | 60.82 | 8.22 | 3.94 | 9.02 |
| Found | 60.92 | 8.44 | 4.03 | 9.25 |

I.R. spectrum (KBr) ν(cm⁻¹): 3370, 2980, 2940, 1720, 1660, 1500, 1300, 1220, 1150, 1090, 1020, 800, 790, 740.

NMR spectrum (δ, CDCl₃) p.p.m.=6.5 (1H, sa); 4.4 to 3.8 (4H+1H, m); 2.9 to 2.5 (2H+2H, 2t); 2.3 (6H, s); 1.4 to 0.7 (13H, t+m.).

EXAMPLE 9

2-(phenylthio)ethyl-2,6-dimethyl-5-ethoxycarbonyl-4-methyl-1,4-dihydropyridin-3-carboxylate

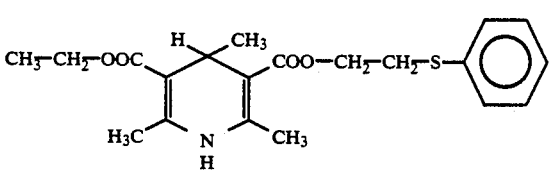

(A) 2-(phenylthio)ethyl-acetylacetate 28.5 ml (31.24 g, 0.37 moles) of diketene are added drop by drop and with stirring to a mixture made up of 50 ml (57.30 g; 0.37 moles) of 2-hydroxyethylphenylsulfide and 0.4 ml triethylamine previously heated to 80° C. The rate of addition is adjusted so that the temperature is kept between 85°-90° C. Once the adding has ended the reaction mixture is kept at 90° C. for 3 hours with stirring. The desired product is isolated by reduced pressure distillation of the previous mixture, resulting in a colorless liquid; melting point: 143°-5° C./0.5 Torr. The yield of the reaction is 86%.

I.R. spectrum (NaCl) ν(cm⁻¹): 3060, 2950, 1750, 1720, 1650, 1580, 1480, 1440, 1360, 1320, 1150, 1020, 740, 690.

NMR spectrum (δ, CDCl₃) p.p.m.=7.2 (5H, m); 4.2 (2H, t); 3.3 (2H, s); 3.1 (2H, t); 2.1 (3H, s.).

(B) 2-(phenylthio)ethyl-2,6-dimethyl-5-ethoxycarbonyl-4-methyl-1,4-dihydropyridin-3-carboxylate A mixture made up of 10 g (0.04 moles) of 2-(phenylthio) ethyl-acetylacetate, 5.42 g (0.04 moles) of ethyl-3-aminocrotonate and 2.4 ml (1.85 g; 0.04 moles) of acetaldehyde in 45 ml of ethanol, is heated to reflux with stirring for 10 hours. After evaporation of 25 ml of the solvent at reduced pressure and cooling of the resulting solution to −10° C., a crystalline yellow solid is obtained; melting point: 80°-2° C. (recrystallized in ethanol.) The yield of the reaction is 49%.

| Analysis for C₂₀H₂₅NO₄S | | | | |
|---|---|---|---|---|
| | % C | % H | % N | % S |
| Calculated | 63.98 | 6.71 | 3.73 | 8.54 |
| Found | 64.15 | 7.01 | 3.77 | 8.27 |

I.R. spectrum (KBr) ν(cm⁻¹): 3340, 2950, 1690, 1640, 1480, 1380, 1290, 1210, 1130, 1050, 770, 720, 680.

NMR spectrum (δ, CDCl₃) p.p.m.=7.2 (5H, m); 6.8 (1H, sa); 4.4 to 3.8 (4H+H, m); 3.2 (2H, t); 2.2 (6H, s); 1.3 (3H, t); 1.0 (3H, d.).

EXAMPLE 10

2-(phenylthio)ethyl-2,6-dimethyl-4-methyl-5-(2-tetrahydrofurfuryloxycarbonyl)-1,4-dihydropyridin-3-carboxylate

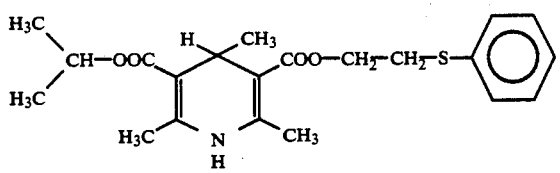

A mixture made up of 15 g (0.06 moles) of 2-(phenylthio) ethyl-acetylacetate (obtained as indicated in example 9,) 3.6 ml (2.77 g; 0.06 moles) of acetaldehyde and 11.66 g (0.06 moles) of 2-tetrahydrofurfuryl-3-aminocrotonate in 60 ml. of absolute ethanol is heated to reflux with stirring for 12 hours. At the end of said time, the resulting solution is purified by passing through activated carboninfusoria earth (1:1) and then the solvent is removed at reduced pressure. In this way the product is obtained in the form of a yellow oil. The yield of the reaction is 65%.

I.R. spectrum (NaCl) ν(cm⁻¹): 3360, 3100, 2980, 2880, 1700, 1670, 1630, 1500, 1450, 1390, 1310, 1280, 1230, 1150, 1110, 1060, 1000, 780, 750, 700.

NMR spectrum (δ, CDCl₃) p.p.m.=7.2 (5H, m); 5.7 (1H, sa); 4.4 to 3.6 (8H, m); 3.2 (2H, t); 2.2 (6H, s); 2 to 1.7 (4H, m); 1.0 (3H, d.).

EXAMPLE 11

2-(phenylthio)ethyl-2,6-dimethyl-5-isopropoxycarbonyl-4-methyl-1,4-dihydropyridin-3-carboxylate

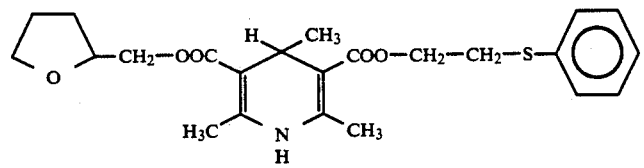

A mixture made up of 15 g (0.06 moles of 2-(phenylthio) ethyl-acetylacetate (obtained as indicated in example 9,) 9.01 g (0.06 moles) of isopropyl 3-aminocrotonate and 3.6 ml (2.77 g; 0.06 moles) of acetaldehyde in 60 ml. of absolute ethanol, is heated to reflux with stirring for 12 hours. At the end of said time, the resulting solution is purified by passing through activated carbon-infusoria earth (1:1) and finally the solvent is removed at reduced pressure. In this way the product is obtained in the form of a pale yellow oil. The yield of the reaction is 67%.

I.R. spectrum (NaCl) ν(cm⁻¹): 3350, 3100, 2980, 1700, 1670, 1500, 1450, 1390, 1300, 1280, 1230, 1150, 1110, 1060, 780, 740, 700.

NMR spectrum (δ, CDCl₃) p.p.m.=7.2 (5H, m); 6.0 (1H, sa); 5.0 (1H, h); 4.3 (2H, t); 3.8 (1H, c); 3.2 (2H, t); 2.2 (6H, s); 1.3 (6H, d); 1.0 (3H, d.).

EXAMPLE 12

2-(phenylthio)ethyl-2,6-dimethyl-4-methyl-5-methoxycarbonyl-1,4-dihydropyridin-3-carboxylate

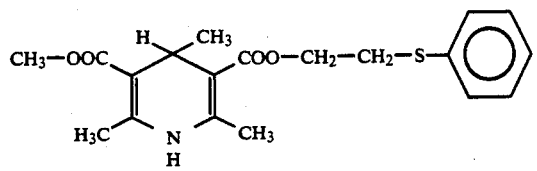

A mixture made up of 15 g (0.06 moles) of 2-(phenylthio) ethyl-acetylacetate (obtained as indicated in example 9,) 3.6 ml (2.77 g; 0.06 moles) of acetaldehyde and 7.25 g (0.06 moles) of methyl 3-aminocrotonate in 60 ml of absolute ethanol is heated to reflux with stirring for 12 hours. At the end of said time, the solvent is evaporated at reduced pressure and the resulting oil is subjected to purification by column chromatography (adsorbent: Silicagel 60, "Merck;" Eluent: Toluene-/Acetone (9:1).) In this way a white solid is obtained; melting point: 69°-71.5° C. The yield of the reaction is 59%.

I.R. spectrum (KBr) ν(cm⁻¹): 3350, 2950, 1700, 1650, 1500, 1440, 1300, 1220, 1140, 1100, 1060, 780, 740, 700, 690.

NMR spectrum (δ, CDCl₃) p.p.m.=7.2 (5H, m); 6.3 (1H, sa); 4.3 (2H, t); 3.9 to 3.6 (1H+3H, m+s); 3.2 (2H, t); 2.2 (6H, s); 1.0 (3H, d.).

PHARMACOLOGICAL STUDIES

1. Studies on Washed Platelets 1.1. Aggregation

The suspensions of washed platelets were obtained from the blood of rabbits (male, albino, New Zealand) anticoagulated with a citric acid-dextrose solution in the proportion 1:6 (v:v.)

The platelet rich plasma (PRP) was obtained by centrifuging the blood samples at 100×g for 10 minutes and the platelet suspensions by centrifuging the PRP at 1,800×g for 15 minutes at 4° C. The pellet thus obtained was washed twice with Tyrode buffer containing citric acid, PGE₁ and apirase, pH 6.5. The platelets thus washed were finally resuspended in Hepes-Tyrode buffer, pH 7.35, supplemented with bovine albumin serum at 0.35%; Ca⁺⁺2 mM. The final concentration of platelets was adjusted to 300,000 platelets/μl. The aggregation was measured turbidimetrically using a lumiaggregometer (Chrono-Log Co., Haventon, Pa., USA) at 37° C. under stirring at 1,100 r.p.m. The study was also carried out on aliquots of PRP pre-incubated with the compounds under study at 37° C. for 5 minutes. The concentration of the antagonists were in all cases 10 μM and aggregation was induced by adding L-PAF diluted in 5 μl of Hepes buffer/albumin, with a final concentration 1.9×10⁻⁹M.

1.2. Release reaction

The platelet secretion was measured in the presence of luciferin/luciferase with ATP release in accord with the method described by Feinman et al. (1977.)

2. Studies on Anesthetized Rats

Hypotension induced by an intravenous injection of PAF-aceter.

Male Sprague-Dawley rats anesthetized with pentobarbital (50 mg/kg., intraperitoneally) were used. 5 mg/kg of the compounds under study were administered intravenously three minutes after injecting PAF-aceter (0.66 μg/kg.) The changes in the average blood pressure were observed for 30 minutes.

TABLE 1

EFFECT ON AGGREGATION AND RELEASE REACTION INDUCED BY 1-PAF ON RABBIT PLATELETS

| COMPOUND ACCORDING TO EXAMPLE | % INHIBITION | |
| --- | --- | --- |
| | AGGREGATION | RELEASE REACTION |
| 1 | 44 | 96 |
| 2 | 26 | 75 |
| 3 | 21 | 78 |
| 4 | 32 | 89 |
| 5 | — | — |
| 6 | 32 | 89 |
| 7 | 14 | 50 |
| 8 | 30 | 69 |
| 9 | 100 | 100 |
| 10 | 11 | 49 |
| 11 | 33 | 89 |
| 12 | 100 | 100 |

The data are the average of six experiments carried out in triplicate. Concentration of 1-PAF=1.92 nM. The concentration of the compounds was in all cases 10 μM. Pre-incubation time: 5 minutes.

INHIBITORY EFFECT ON HYPOTENSION INDUCED BY 1-PAF ON ANESTHETIZED RATS

| COMPOUND ACCORDING TO EXAMPLE | % INHIBITION OF HYPOTENSION | |
| --- | --- | --- |
| | 3 min.* | 20 min.* |
| 1 | 9 | 0 |
| 2 | 14 | 51 |
| 3 | −19[a] | 0 |
| 4 | 5 | 33 |
| 5 | — | — |
| 6 | 21 | 30 |
| 7 | −31[a] | −82[a] |
| 8 | −38[a] | −115[a] |
| 9 | 32 | 30 |
| 10 | 8 | 36 |
| 11 | 0 | 18 |
| 12 | 61 | 57 |

The data are the average of 5 experiments. The dose of compound administered intravenously was in all cases 5 mg/kg.
*1-PAF (0.66 μg/kg) was injected 3 and 20 minutes before the intravenous injection of the compounds
[a]The products increased hypotension induced by 1-PAF.

We claim:

1. 4-alkyl-1,4-dihydropyridines with PAF-antagonist activity of formula I

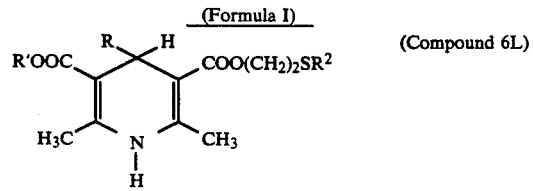

(Formula I) (Compound 6L)

wherein

R is a $C_1$–$C_4$ saturated straight or branched chain alkyl group,

R' is selected from the group consisting of a $C_1$–$C_6$ saturated straight or branched chain alkyl group, a $C_1$–$C_6$ saturated straight or branched chain alkyl interrupted by an oxygen atom, and the 2-tetrahydrofurfuryl group, $R^2$ is a $C_1$–$C_4$ saturated straight chain alkyl group or a phenyl group, wherein R is methyl, R' is ethyl and $R^2$ is phenyl is excluded from said formula I.

2. A compound according to claim 1, selected from among the following:

a) 3-(ethylthio)ethyl-2,6-dimethyl-4-methyl-5-methoxycarbonyl-1,4-dihydropyridin-3-carboxylate, b) 3-(methylthio)ethyl-2,6-dimethyl-4-methyl-5-methoxycarbonyl-1,4-dihydropyridin-3-carboxylate, c) 3-(methylthio)ethyl-2,6-dimethyl-5-ethoxycarbonyl-4-methyl-1,4-dihydropyridin-3-carboxylate, d) 3-(ethylthio)ethyl-2,6-dimethyl-5-ethoxycarbonyl-4-methyl-1,4-dihydropyridin-3-carboxylate, e) 3-(methylthio)ethyl-2,6-dimethyl-4-methyl-5-(2-methoxyethoxycarbonyl)-1,4-dihydropyridin-3-carboxylate, f) 3-(methylthio)ethyl-2,6-dimethyl-4-ethyl-5-ethoxycarbonyl-1,4-dihydropyridin-3-carboxylate, g) 3-(methylthio)ethyl-2,6-dimethyl-5-ethoxycarbonyl-4-n-propyl-1,4-dihydropyridin-3-carboxylate, h) 3-(ethylthio)ethyl-2,6-dimethyl-5-ethoxycarbonyl-4-n-propyl-1,4-dihydropyridin-3-carboxylate, i) 3-(phenylthio)ethyl-2,6-dimethyl-4-methyl-5-(2-tetrahydrofurfuryloxycarbonyl)-1,4-dihydropyridin-3-carboxylate, j) 3-(phenylthio)ethyl-2,6-dimethyl-5-isopropoxycarbonyl-4-methyl-1,4-dihydropyridin-3-carboxylate k) 3,6-(phenylthio)ethyl-2,6-dimethyl-4-methyl-5-methoxycarbonyl-1,4-dihydropyridin-3-carboxylate.

3. The compound according to claim 1, wherein R' is 2-tetrahydrofurfuryl group.

* * * * *